United States Patent
Bronstein et al.

(10) Patent No.: US 7,053,208 B2
(45) Date of Patent: May 30, 2006

(54) DIOXETANE LABELED PROBES AND DETECTION ASSAYS EMPLOYING THE SAME

(75) Inventors: Irena Bronstein, Newton, MA (US); Brooks Edwards, Cambridge, MA (US); Christopher Martin, Bedford, MA (US); John Voyta, Sudbury, MA (US)

(73) Assignee: Applera Corporation, Bedford, MA (US)

( * ) Notice: Subject to any disclaimer, the term of this patent is extended or adjusted under 35 U.S.C. 154(b) by 426 days.

(21) Appl. No.: 10/083,474

(22) Filed: Feb. 27, 2002

(65) Prior Publication Data

US 2002/0106687 A1    Aug. 8, 2002

Related U.S. Application Data

(63) Continuation of application No. 09/340,726, filed on Jun. 29, 1999, now Pat. No. 6,451,531, which is a continuation of application No. 09/018,180, filed on Feb. 3, 1998, now Pat. No. 6,063,574, which is a continuation of application No. 08/767,479, filed on Dec. 16, 1996, now Pat. No. 5,800,999.

(51) Int. Cl.
*C12Q 1/68* (2006.01)
*C07H 21/00* (2006.01)
*C12M 1/00* (2006.01)
*C12M 1/34* (2006.01)
*C12M 3/00* (2006.01)

(52) U.S. Cl. .............. 536/26.6; 435/6; 435/283.1; 435/287.1; 435/287.2; 435/288.3; 435/288.7

(58) Field of Classification Search .............. 435/6, 435/283.1, 287.1, 287.2, 288.3, 288.7; 536/24.4, 536/26.6
See application file for complete search history.

(56) References Cited

U.S. PATENT DOCUMENTS

| | | | | |
|---|---|---|---|---|
| 4,794,073 A | * | 12/1988 | Dattagupta et al. | 435/6 |
| 5,672,514 A | * | 9/1997 | Tsuchiya et al. | 436/86 |
| 5,800,999 A | * | 9/1998 | Bronstein et al. | 435/6 |
| 6,143,514 A | * | 11/2000 | Ullman et al. | 435/28 |
| 6,451,531 B1 | * | 9/2002 | Bronstein et al. | 435/6 |

OTHER PUBLICATIONS

Lipschutz et al., "Using Oligonucleotide Probe Arrays to Access Genetic Diversity", Biotechniques, vol. 19, pp. 442-446 (1995).*

Eggers et al. A microchip for quantitative detection of molecules utilizing luminescent and radioisotope reporter groups. BioTechniques vol. 17, No. 3 1994, paes 516-525.*

* cited by examiner

*Primary Examiner*—Jezia Riley
(74) *Attorney, Agent, or Firm*—Merchant & Gould

(57) ABSTRACT

Probes labeled with 1,2-dioxetane precursors can be employed in a variety of assays. The probes may be nucleic acid, peptide nucleic acid, proteins including enzyme, antibody or antigen, steroid, carbohydrate, drug or non-drug hapten. The probe is provided with a 1,2-dioxetane precursor bound thereto, generally either covalently, or a strong ligand bond. The dioxetane precursor moiety is converted to a bound 1,2-dioxetane by exposure to singlet oxygen. These dioxetane (labels) either spontaneously decompose, or are induced to decompose by an appropriate trigger to release light. The trigger may be a change in pH temperature, or an agent which removes a protective group. Assay formats in which these 1,2-dioxetane labeled probes and referents may be used to include hybridization assays, immuno assays, gel-based assays and Capillary Zone Electrophoresis.

20 Claims, 1 Drawing Sheet

DIOXETANE LABELED PROBES AND DETECTION ASSAYS EMPLOYING THE SAME

This application is a continuation of U.S. patent application Ser. No. 09/340,726, filed Jun. 29, 1999 (now U.S. Pat. No. 6,451,531), which is a continuation of U.S. patent application Ser. No. 09/018,180, filed Feb. 3, 1998 (now U.S. Pat. No. 6,063,574), which is a continuation of U.S. patent application Ser. No. 08/767,479, filed Dec. 16, 1996 (now U.S. Pat. No. 5,800,999). The entirety of these patent applications are incorporated herein by reference.

BACKGROUND OF THE INVENTION

Field of the Invention

This invention pertains to probes labeled with precursors of 1,2-dioxetanes, which, after sequence specific linkage detection or hybridization with target complementary nucleic acid in a biological sample, can be photooxidized to form 1,2-dioxetanes which subsequently decompose to release light. The light emission is an indication of the presence, in the sample tested, of the target nucleic acid. This invention also pertains to proteins labeled with precursors to 1,2-dioxetanes which are used to quantitate the level of analytes. This invention also pertains to non-biological probes labeled with precursors to 1,2-dioxetanes which are used to detect the presence of analyzes in a sample. Probes labeled with precursors and dioxetanes, as well methods of making these probes are also addressed. Nucleic acids, peptide nucleic acids, proteins, steroids, carbohydrates, drugs and other haptens may be identified by these assays.

BACKGROUND OF THE INVENTION

This invention pertains to assays for the detection of particular target nucleic acid sequences and specific protein, carbohydrate, steroid and hapten analytes in a sample to be inspected. This application is assigned to Tropix, Inc., a leader in chemiluminescent assays, and reagents therefor. The common assignee has pioneered the development and patenting of 1,2-dioxetane chemiluminescent substrates for use in the detection of target analytes of a sample, including immunological assays of a wide variety. While the list of patents is exhaustive, prominent patents include U.S. Pat. Nos. 5,112,960 and 5,538,847, which disclose dioxetanes particularly adapted for improved assay properties, as well as U.S. Pat. Nos. 5,145,772 and 4,978,614 which disclose methods of enhancing the intensity of chemiluminescence obtained from these chemiluminescent molecules. As broadly described, these dioxetane molecules have the structure set forth below.

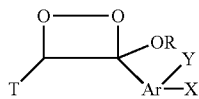

In these 1,2-dioxetanes, T is a stabilizing group. Because the dioxetane molecule, without the stabilizing group, may spontaneously decompose, a group, typically a polycycloalkyl group is bound to the dioxetane to stabilize it against spontaneous decomposition. This need for stabilization has resulted in commercially developed 1,2-dioxetanes being generally spiroadamantyl. The adamantyl group, spiro-bound, can be substituted at any bridge head carbon, to affect chemiluminescent properties. As indicated, the remaining carbon of the dioxetane ring bears a OR substituent, wherein R is generally an alkyl or cycloalkyl, although it may be a further aryl group. Preferred embodiments include substituted alkyls, with the substituent including halogenated groups, such as polyhaloalkyl substituents. The remaining valence is occupied by an aryl moiety, preferably phenyl or naphthyl. If naphthyl, particular substitution profiles on the naphthyl ring are preferred. See, e.g., U.S. Pat. No. 4,952,707. The aryl ring bears at least one substituent, X. In commercially developed dioxetanes, this is an enzyme-cleavable group. For instance, many assays employ an exogenous enzyme, such as alkaline phosphatase, to ensure reliability of the assay. The enzyme is typically conjugated to a binding ligand, either an antibody, a nucleic acid fragment, or similar binding pair member, which will bind to the target substance to be detected. Where the conjugated enzyme is alkaline phosphatase, the enzyme-cleavable group X will be a phosphate. The aryl ring may also bear a substituent Y, which is selected to be either electron donating, or electron withdrawing. Preferred groups include chlorine, alkoxy and heteroaryl, although other groups may be employed. These substitutions further effect chemiluminescent properties, and reaction kinetics. A wide variety of other substituents are disclosed in the afore-referenced patents, all of which are incorporated herein by reference.

Uniformly, these dioxetanes are disclosed as useful enzyme substrates, that is, the binding pair member conjugated to an enzyme is allowed to bind to the target analyte, and after washing to remove unbound material, the dioxetane is added. In the presence of the conjugated enzyme, the protective group is cleaved, leading to decomposition of the dioxetane, and light emission. These dioxetanes provide a variety of valuable properties for the detection of biomolecules that had not been previously available. These include detection sensitivity, thermal stability, water solubility and ease of use. Employing the enzyme amplification factor, the dioxetanes commercially available offer the highest detection sensitivity attainable in commercialized assays. Similarly, the thermal stability of the described dioxetanes is superior to that of radioisotopes, fluorophores and other available chemiluminescent systems. Because biological assay conditions generally employ an aqueous media, water solubility, an important criteria, was met by use of the dioxetane substrates, which proved easy to use in both qualitative and quantitative determinations, in solutions, and in blotting assays.

Increasingly, however, PCR-amplified probe hybridization assays, or in-situ applications, are receiving commercial attention. Enzyme labels, a prerequisite for use of the enzyme-cleavable dioxetanes described, may not always be appropriate for such assays. For example, a short oligonucleotide probe used to detect a specific target nucleic acid sequence is difficult to label with an enzyme. Most enzymes have high molecular weight, are large and may easily interfere with the hybridization of the labeled probe to a target DNA sequence. Further, most enzymes cannot be subjected to the harsh conditions used in processing nucleic acids, such as high temperatures and organic or inorganic solvents.

Further, a wide variety of assays, including in-situ nucleic acid detection, chromosome analysis, protein detection, such as cell-surface antigens and related applications require microscopic analysis, demanding very high resolution capability. Further, the trend in detection methodologies appears to be moving toward miniaturization and high density in order to achieve efficiency, including the use of electromagnetically sensitive surfaces such as semiconductors and microchips. See, e.g., Eggers et al, 516 *BioTechniques, Vol. 17, No. 3* (1994). For these applications, there is a need for light emitters, or other labels, which produce points of light at a very precise location on a microscopic level. This implies a need for immobilized labels which emit light while covalently attached, or otherwise positively bound, to a ligand or binding agent. In contrast, dioxetane enzyme substrates are added to bound enzyme labeled reagents, and are activated by the removal of the cleavable group by the enzyme, which leaves an oxyanion intermediate, which may diffuse randomly, until decomposition, and chemiluminescence, is achieved. While the hydrophobic affinity of the environment may passively "bind" the dioxetane anion, the lack of an attachment of the anion to the probe allows limited diffusion, which limits imaging on a microscopic scale.

Moreover, the high sensitivity required for many immunological assays, met by the enzyme-cleavable dioxetanes described above, may not be necessary with PCR. PCR, and linear target amplification techniques including cycling pre technology (CPT), and oligonucleotide ligase assay (OLA), appear to be the future technology of choice for many nucleic acid detection formats. Since these techniques all offer some degree of amplification, with that of PCR being generally considered the greatest, ease of use, potential for an homogenous assay and universality may be features that are selected over label sensitivity.

Further, the use of nucleic acid probes and the like for assays implies a set of conditions that may be unlike those for which the enzyme-cleavable dioxetanes were originally developed. Thus, water solubility may not be required. For chemiluminescently labeled detection of nucleic acids, water solubility is not critical. A partial or total use of solvents is not only possible, but it may dramatically enhance the chemiluminescent efficiency of the label (it is well established that in many organic solvents, chemiluminescent efficiency of the aryl-substituted 1,2-dioxetane decomposition is improved).

Thus, there remains a need in the industry to develop chemiluminescent dioxetane labels for nucleic acid probes and related technologies that can provide high signal resolution, resistance to hybridization conditions, and reliable emission properties as labels in a nucleic acid assay.

SUMMARY OF THE INVENTION

The above objects, and others made more clear through the discussions set forth below, are achieved by the provision of probes bearing a 1,2-dioxetane precursor (generally enol ether or phosphonate ester) bound thereto. The probe may be a nucleic acid or peptide nucleic acid, either for hybridization assays or sequence analysis, where the target for inspection may itself be labelled. Alternatively, the probe may comprise an antibody specific for a protein, steroid or carbohydrate target, or an antigen which binds a target antibody, such as an autoantibody. Additionally, reference components, such as drugs, non-drug haptens, etc. may be labelled for use in assays. In nucleic acid probes, the dioxetane precursor may be conveniently bound to the probe covalents either through an amino- or thiol-containing side chain after formation of the probe, or as part of the sequencing synthesis of the probe. The precursor remains present on the probe throughout hybridization, including the high temperatures and use of complex buffers that typically accompany harsh hybridization conditions. After repeated washing to remove non-bound material, the dioxetane precursor is photooxygenated, either through the use of a sensitizer suspended in solution, provided with molecular oxygen and visible light, or by an intercalating dye which is allowed to intercalate after hybridization, followed by irradiation in the presence of molecular oxygen. In either fashion, singlet oxygen is produced by the sensitizer, and the precursor is photooxygenated to generate a dioxetane. The dioxetane is then caused, or allowed, to decompose, emitting light. The half-life of the dioxetane need not be long, and accordingly, the adamantyl group need not be employed. In place of the adamantyl group, branched alkyl groups, of, e.g., 1–6 carbon atoms, or any other group that does not interfere with the formation and subsequent decomposition of the dioxetane, can be employed. Upon formation of the dioxetane, if it does not decompose and chemiluminesce spontaneously, a variety of conditions can be selected to "activate" the dioxetane, that is, cause it to decompose and chemiluminesce. Preferred conditions to be altered would include PH or temperature. Other assay formats, taking advantage of the other (non-nucleic acid) labeled probes employ these chemiluminescent labels to advantage in similar systems.

DETAILED DESCRIPTION OF THE INVENTION

Figure 1:
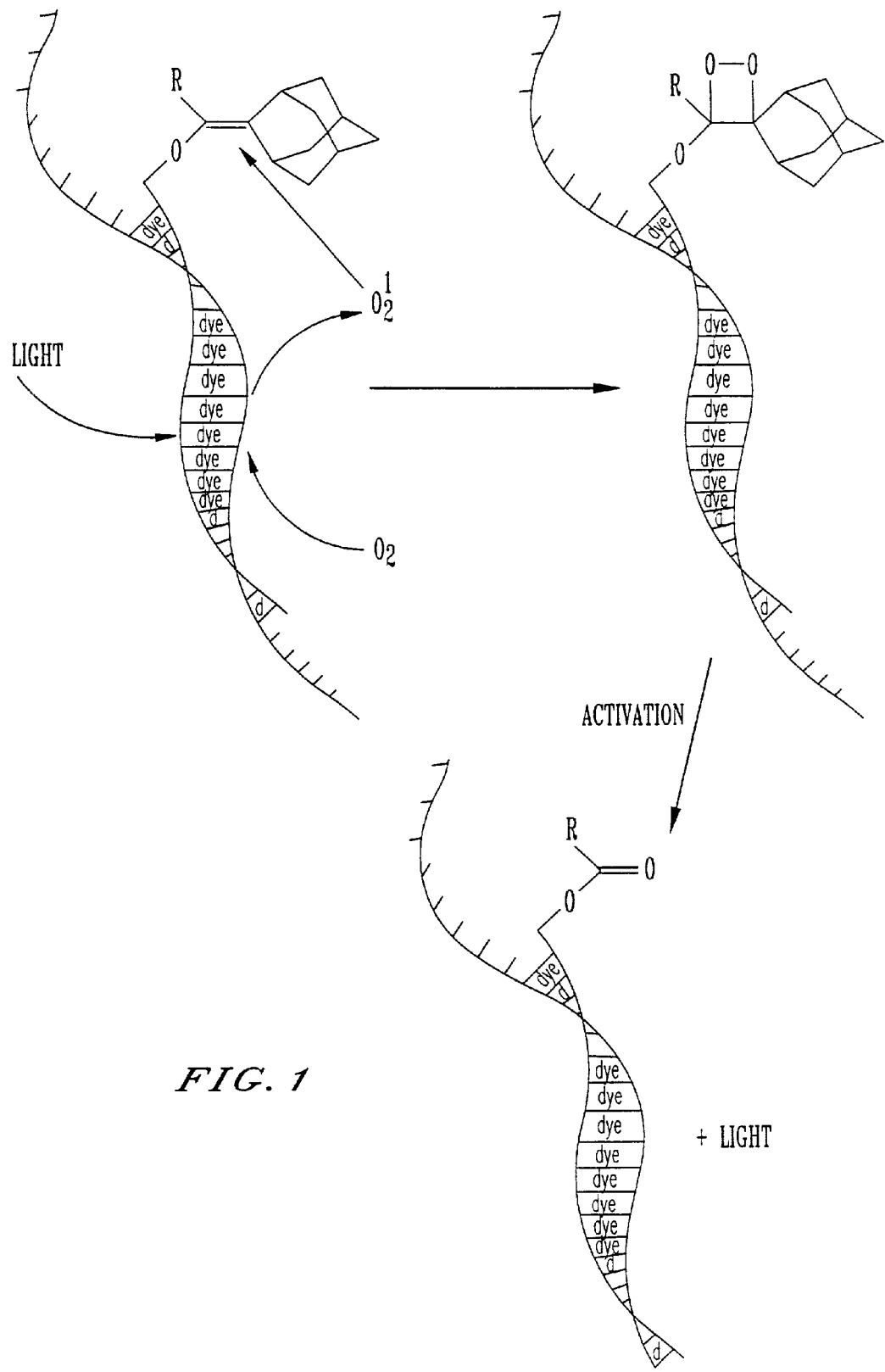
FIG. 1 illustrates, schematically, the use of an intercalating dye to produce singlet oxygen to photooxygenate an enol ether dioxetane precursor, into a dioxetane, which is then triggered to release light.

This invention is described below, by reference to specific examples. Except where indicated, specific examples are not intended to be limiting, and can be broadly generalized by those of skill in the art without the exercise of inventive faculty, to broadly embrace alternatives within the scope of the claims presented below.

Nucleic acid probes are widely used in hybridization assays, either directly, or in conjunction with PCR amplified assays. A nucleic acid probe consists of a linked sequence of nucleotide bases. One object of the invention is to provide probes of this type which bear at least one dioxetane precursor bound thereto, preferably through a linker group. The precursor as illustrated below is typically an enol ether or phosphonate ester. This precursor can be represented by the general formula:

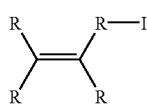

I

The dioxetane precursor labels useful in this invention are reactive with singlet oxygen produced from either a photochemical, chemical or thermal reaction. The olefins used for this reaction can be represented by the general structure I above, where R is a carbon-containing group which may also contain oxygen, nitrogen or sulfur, which can be selected independently from the group consisting of alkyl, heteroalkyl, heteroaryl, heteroaralkyl, aryloxy, hydrogen, aryl, substituted aryl, hydroxyaryl or substituted hydroxyaryl, acyloxyaryl or substituted acyloxyaryl, siloxyaryl or substituted siloxyaryl, aminoaryl or substituted aminoaryl, and sulfonamidoaryl or substituted sulfonamidoaryl. Any of these R groups may be joined together to form one or more rings either on one side of the double bond, or across the double bond. The linking of the R groups may be through a bond, or through a bridge which may be a heteroatom or a carbon containing group optionally containing one or more heteroatoms. Preferably, one of the R groups is an electron donating group, attached directly to the olefin or through conjugated double bonds. Enol ethers, enediol ethers, vinyl sulfides, enamines, and N-acylenamines are examples of olefins useful in the invention, which contain at least one heteroalkyl substituent which is bonded to an olefinic carbon in such a way that the heteroatom is attached directly to the double bond. Exemplary olefinic systems suitable for use in the invention may be found in U.S. Pat. No. 5,516,636, incorporated by reference, and published European Patent Application 0 515 194 A2, see, e.g., Formulas 1–13, pages 24–29. However, the olefins of this invention bear an additional group X as indicated in structure I. In this formula, X is a linking group, or a direct bond to a nucleic acid probe forming a covalent bond to the dioxetane precursor and ultimately the dioxetane for pinpoint resolution and accuracy. Any linker function which maintains the ability of the probe to recognize its target may be utilized. Preferably x is a linking alkyl group of 1–11 carbon atoms, which may be attached to any of the R groups through a carbon-carbon or carbon-heteroatom bond, further comprising terminal amino or N-aminoalkyl amide groups for ease of attachment. More preferably, X is a linking alkyl group of 1–6 carbon atoms further comprising a terminal amino group for ease of attachment. R groups are independently selected from a wide variety of substituents. Preferred substituents include aryl groups, such as phenyl and naphthyl groups, oxy groups of the formula YO—, wherein Y is aryl, alkyl, aralkyl, cycloalkyl, etc. Each of the R groups may also be alkyl, however, since the dioxetane is to be preferably produced by photooxygenation of the enol ether across the double bond, as a general selecting principle, each R should preferably be selected such that there is no proton in the allylic group position. However, some alkyl groups may not interfere with the photooxygenation, particularly in polar solvents. Alkyl groups may be selected for one or more of the positions of the R groups, provided the alkyl groups are branched at the point of attachment to the double bond. Thus, —C(CH$_3$): groups may be used in connection with the general formula set forth above.

Preferably, at least one R group is a YO— group, as the presence of the oxygen promotes dioxetane formation. Where none of the R groups is an oxy group, dioxetane formation may proceed at a prohibitively slow pace.

Each of the R groups may be substituted with optional substituents, including halogens, amines, alkoxy, heteroaryl, e.g., benzothiazol moieties and the like. Synthesis and attachment to a base moiety of a probe, is illustrated in the following synthesis scheme. One or more of the R groups may comprise an auxiliary fluorophore, such as those recited in U.S. Pat. No. 5,112,960 incorporated herein-by-reference, including anthracenes, rhodamines, flyoescins, coumarins, erythrosins, acridines, pyrenes, stilbenes, nitrobenzoxadiazoles, quinolines, acidoacridines, carbazoles, flyorescent cyanines, carbocyanines, pyridinium salts, oxonols, resorting, and derivatives of these groups, as well as phenyl and naphthyl moieties.

Further, one of the R groups may bear a protective group which, if removed, induces decomposition of the dioxetane group formed from the precursor. These include corresponding enzyme-labile substrates, such as phosphates and others set forth in U.S. Pat. No. 5,112,960, and groups which may be removed by addition of non-enzymatic chemicals, such as base, electron donors, etc. Among the latter are OH group, tri-substituted silyl groups, etc.

Synthesis of 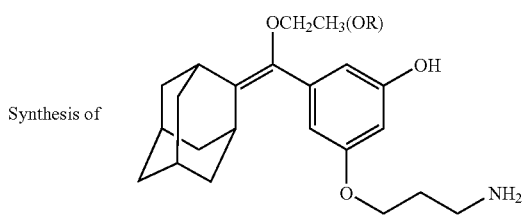

The synthesis is conducted using the Wittig-Horner reaction of a properly substituted phosphonate ester with 2-adamantanone, a substituted 2-adamantanone, or any other ketone (e.g.diisopropyl ketone) may be used in the condensation as well. The phosphonate ester ultimately derives from an aldehyde as described in U.S. Pat. No. 5,225,584:

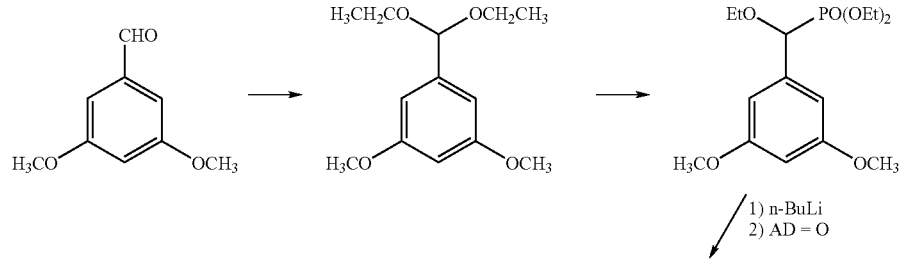

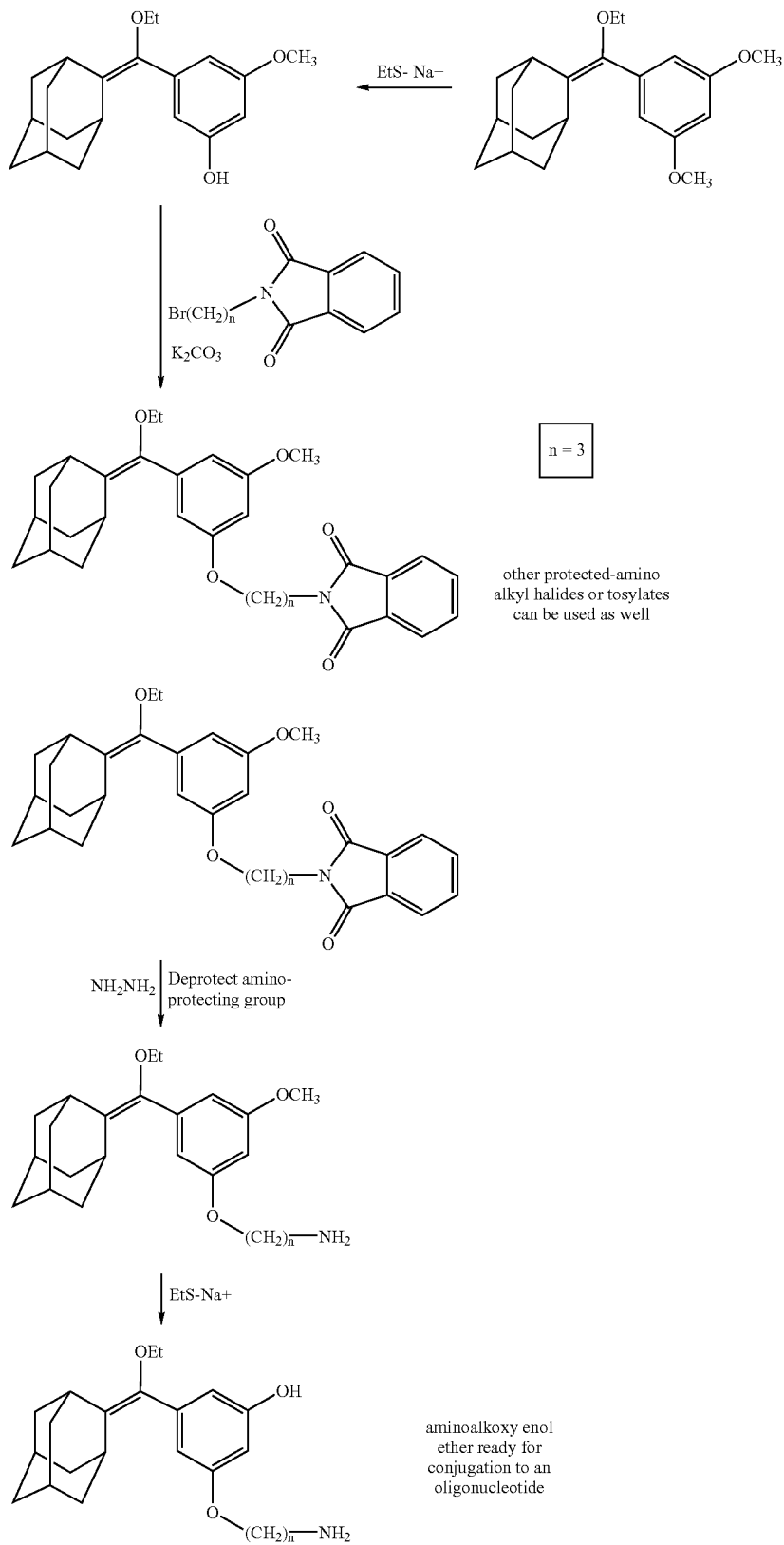

Alternatively, the synthesis may proceed through a 3,5-dihydroxyphenyl enol ether which is also obtained using the Wittig-Horner reaction as depicted below, starting with 3,5-dibenzyloxybenzaldehyde:
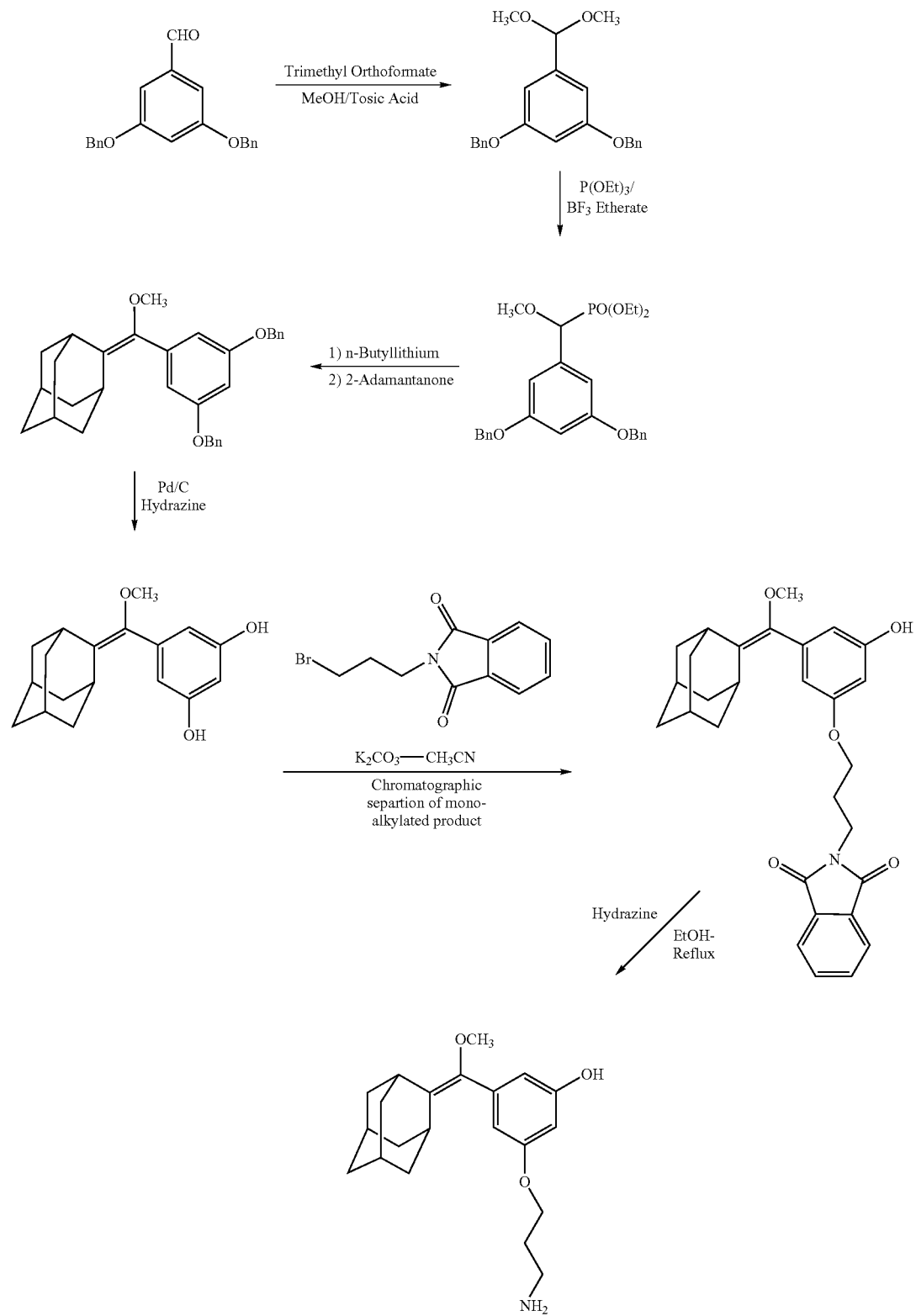

It will be appreciated by those of ordinary skill in the art that the functionalized enol ether may be linked, ultimately through an amino group, which can then be directly cross-linked to the oligonucleotide, through available heterobifunctional cross-linking agents, or homobifunctional cross-linking groups. Thus, in the formula, X may be —ZNH$_2$, wherein Z is an alkyl or alkoxy group bound to the oxygen of the enol ether precursor. These strategies are illustrated below.

Aminoalkyl-substituted olefins

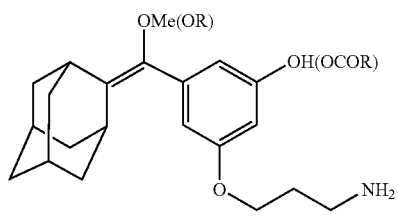

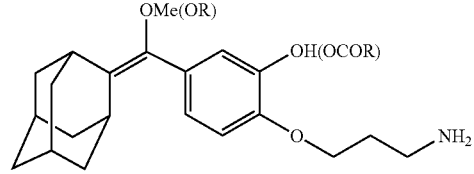

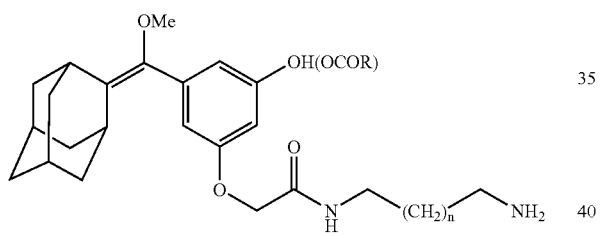

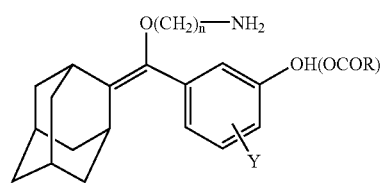

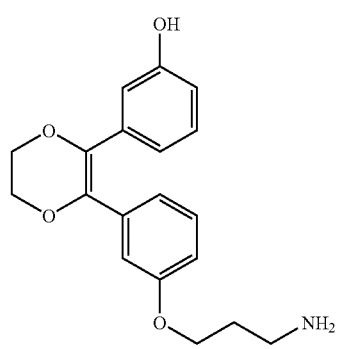

Heterobifunctional crosslinkers (Pierce catalog)

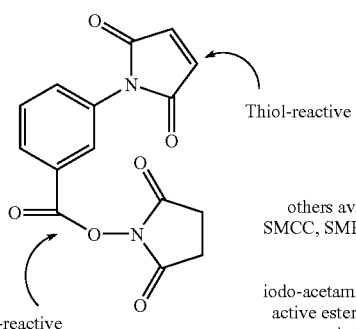

MBS

Thiol-reactive

Amine-reactive others available: SMCC, SMPB, GMBS iodo-acetamido NHS active esters are also suitable Homobifunctional crosslinkers (Pierce catalog)

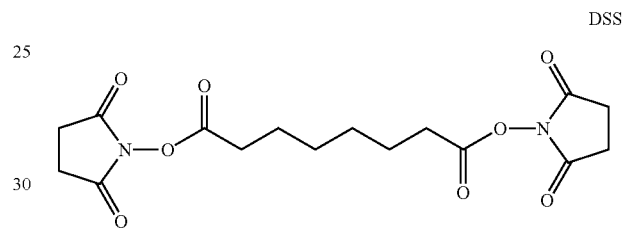

DSS

5' amino or thiol terminated oligo's are commercially available or synthesized on a DNA synthesizer.

HS—[OLIGONUCLEOTIDE]

H$_2$N—[OLIGONUCLEOTIDE]

Assembly of enol ether-labled oligonucleotide

Step 2  HS—[OLIGONUCLEOTIDE]

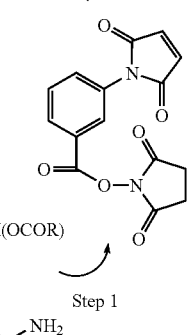

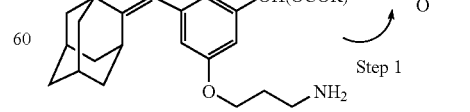

Step 1

Synthesis of Dioxetanes

As described above, the dioxetane precursor may be covalently bound to a probe, to provide a fixed, pinpoint emission of light, such that the dioxetane remnant after decomposition and light emitting fragment (an ester) remains attached to the probe.

In an alternative synthesis methodology, the enol ether, or corresponding precursor, phosphonate ester, is incorporated during the synthesis of the probe. This can be achieved in a DNA synthesizer, where the dioxetane precursor would simply be added as an additional "building block" for a selected oligonucleotide. This approach permits the incorporation of multiple labels onto a single probe. Additionally, precursor incorporation can be either at some place in the middle of the chain, or at the terminal position of the probe. Either labeling of the probe following synthesis, as described above first, or in-synthesis incorporation of the enol ether precursor or phosphonate, is an acceptable alternative.

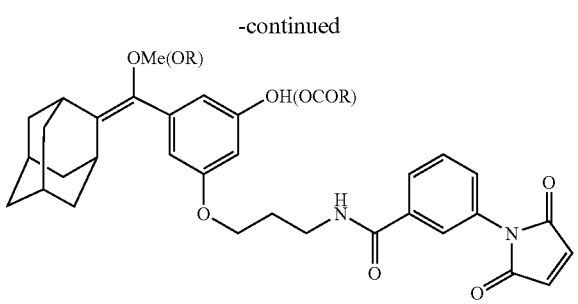

The product of Step 1 could be synthesized independently or in situ-ready for covalent attachment to the thiolated oligoucleotide Exemplary aminoalkyl or aminoalkoxy-substituted olefins

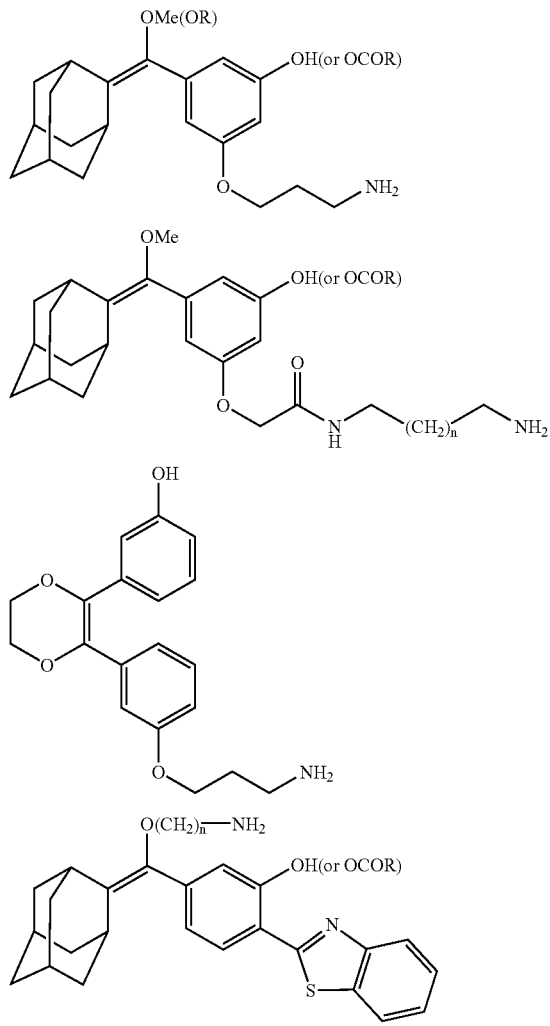
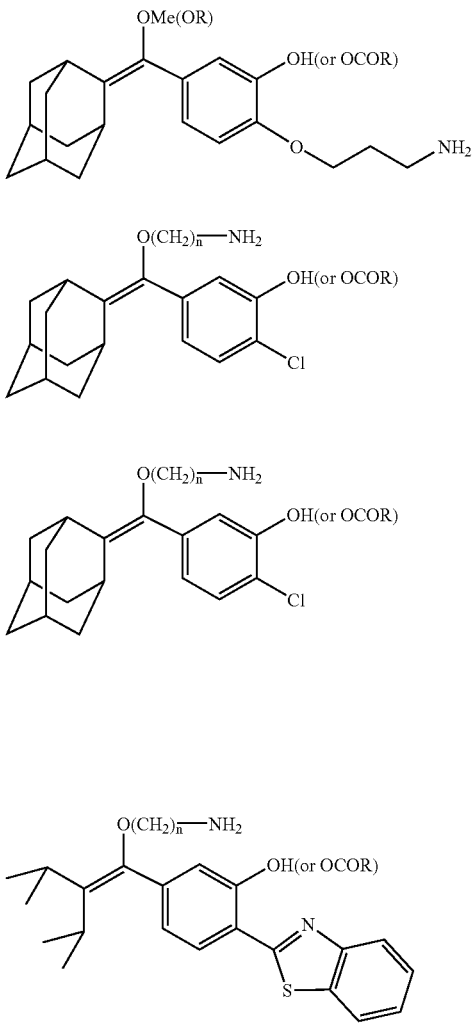

-continued

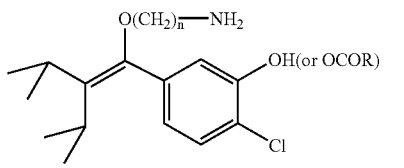

Enol Ether Phosphoramidite for automated synthesis of oligonucleotide probes

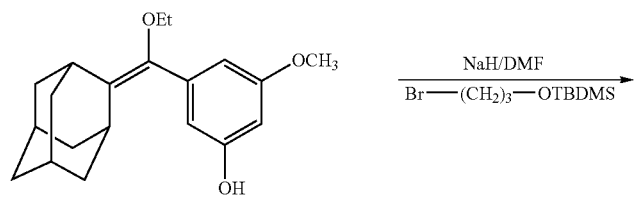

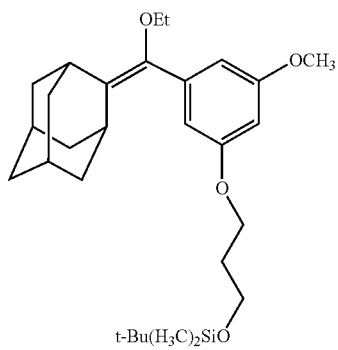

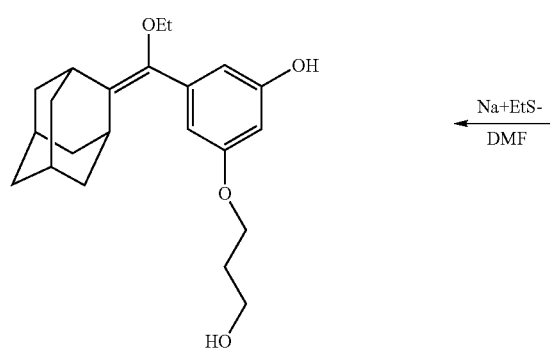

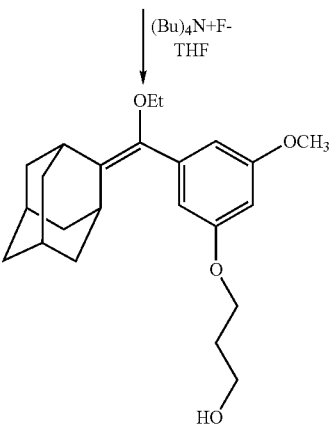

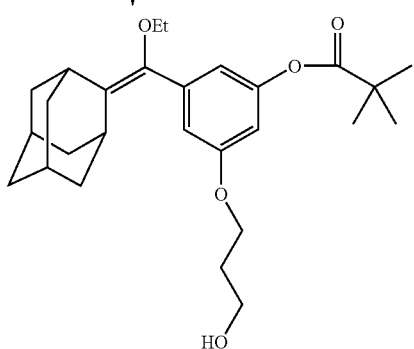

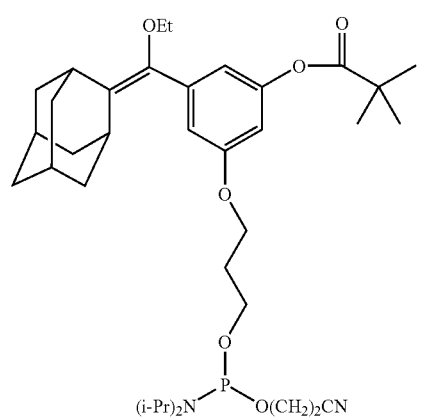

In order to label "long", native nucleic acid probes, the enzymatic processes of nick translation or 3' terminal labeling with terminal transferase are well described in the art. European Patent Application 0 251 786 A3 discloses the utility of alknylamino-nucleotides which can serve as substrates for the enzymes which accomplish the aforementioned processes. The synthesis of 5-(3-amino-1-propynyl)-2'-deoxycytidine 5'-triphosphate is given and is easily extended to other nucleotides containing uridine, 7-deazaguanosine, and 7-deazaadenosine bases. These aminoalkynyl triphosphates are useful starting materials for dioxetane precursor labeled nucleotide triphosphates which can be used for nick translation, random primer or 3'-terminal labeling of DNA probes. One of skill in the art will also recognize that these aminoalkynyl triphosphates as well as aminoallyl deoxynucleoside triphosphates are available as reactants with a diverse range of homobifunctional or heterobifunctional cross-linkers such that the product is reactive with an olefinic dioxetane precursor creating a labeled triphosphate where the linker (or spacer) is chosen so as not to sterically hinder enzymatic incorporation into the probe.

assay. Thus, dioxetane formation can follow all manipulative assay steps. The enol ether precursor is stable with respect to these hybridization conditions, including elevated temperatures and solvents, where the corresponding dioxetane might not be.

Following hybridization, and prior to completing the assay, the dioxetane is formed, preferably through photooxygenation. At least two methods can be selected to photooxygenate the enol ether, and thereby form the dioxetane ring. In one alternative, a sensitizer (e.g., Rose Bengal or any of a wide variety of singlet oxygen generating sensitizers) is

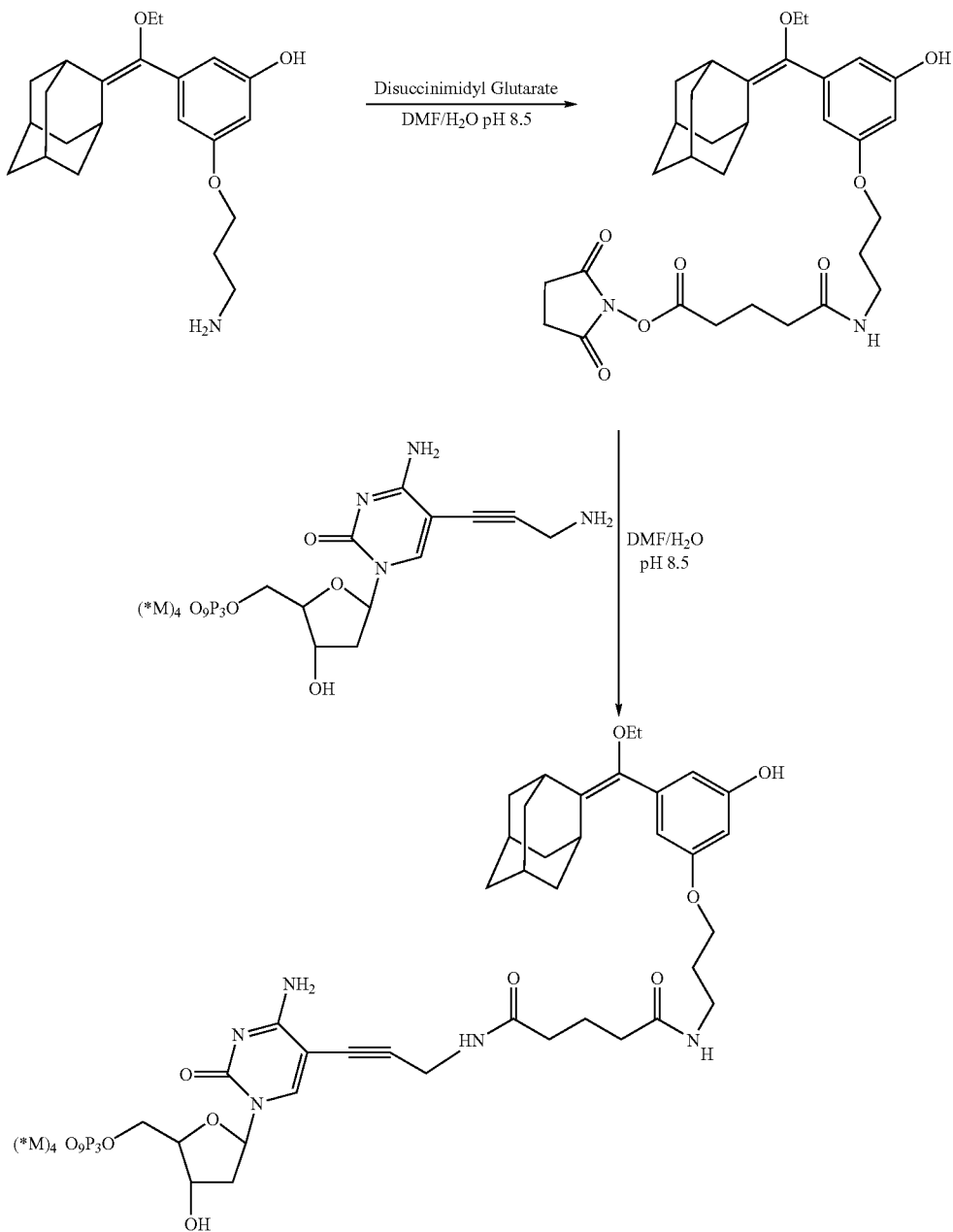

Once the probe is provided with the bound or incorporated label, the probe may be allowed to bind to its complementary target sequence, for instance, in a hybridization assay. provided in a solution in which the precursor-labeled probe is present. Using conventional photooxygenation techniques, that is, the introduction of molecular oxygen and irradiation, e.g., visible light, singlet oxygen is produced which will induce the formation of the dioxetane. See, e.g., U.S. Pat. No. 4,956,477, incorporated by reference herein, and U.S. Pat. No. 4,959,182, column 22, line 30–column 23, line 25, for examples of dioxetane manufacture through this form of photooxygenation.

A suitable sensitizing dye for the invention is any dye which populates the triplet excited state to any extent during photophysical excitation by any appropriate wavelengths of electromagnetic radiation so that the said triplet state may interact with triplet atmospheric oxygen to generate singlet oxygen. A great number of organic dyes are capable of performing this transition, but without limitation the following exemplary compounds include those species most well known in the art: methylene blue and derivatives, rose bengal and derivatives, eosin and derivatives, erythrosin and derivatives, tetraphenyl-porphine and derivatives, buckminsterfullerene and derivatives, bis-acenaphthalene-thiophene and derivatives, hematoporphyrin and derivatives, chlorophyll and derivatives, protoporphyrin and derivatives, methylpyrroporphine and derivatives, tetrakis(1-alkyl-4-pyridyl) porphine salts and derivatives, tetrakis(4-trialkyl-ammonio)-phenyl porphine salts and derivatives. Other classes of suitable dyes include the cyanine dyes, ethidium dyes, acridine dyes or phthalocyanine dyes, especially when substituted with group which facilitate spin-orbit coupling to produce reasonable triplet state yields. The utility of mixtures of two or more triplet sensitizing dyes is also within the scope of the disclosed invention. Cationic triplet dyes are particularly useful for that aspect of the invention which requires intercalation of the sensitizing dye into the nucleic acid hybrids. One of skill in the art will also appreciate the fact that singlet oxygen can be generated from ground state oxygen in the gaseous phase by microwave discharge or by photolysis in the vapor phase with volatile triplet sensitizers such as naphthalene. Dioxetane formation in an olefin-labeled probe nucleic acid hybrid can thus occur in a miniaturized matrix array using a gaseous reagent. Subsequent decomposition and emission of light can be accomplished thermally, or if an alkali sensitive triggering function is present, through the use of a gaseous base such as a volatile amine, or with an alkaline substance in solution. In addition to the photochemical generation of singlet oxygen using dye sensitization either in solution or by way or intercalated triplet sensitizers, the invention also contemplates the use of singlet oxygen generated chemically or thermally. A number of methods are well known including the use of sodium hypochlorite/hydrogen peroxide [*J. Am. Chem. Soc.*, (1969) 3879 3880]; sodium molybdate/hydrogen peroxide [*Tet.Lett.*, (1989)783]; decomposition of phosphite ozonides [*Chem. Comm.*, (1970) 956]; decomposition of endoperoxides [*J. Am. Chem. Soc.*, (1967) 3073; *Tetrahedron*, (1987) 1737; and *J. Am. Chem. Soc.*, (1985) 6329]; and decomposition of tetroxanes [*J. Am. Chem. Soc.*, (1970) 1128] among others.

An alternative means of generating singlet oxygen, and thus photooxygenating the dioxetane, is provided by the use of intercalating dyes. This alternative is illustrated in FIG. 1. FIG. 1 illustrates the dioxetane formation of a spiroadamantyl dioxetane. As noted, this invention does not require the highly stable spiroadamantyl dioxetane, but for ease of reference, as this dioxetane is commercially familiar to those of skill in the art, it is used for exemplification only. After hybridization of a DNA probe labeled with the dioxetane precursor to a target complementary sequence, the sensitizing dye is allowed to intercalate. Although this invention is not so limited, among suitable intercalating dyes are derivatives of tetraphenyl porphine, in which the phenyl rings are replaced by pyridine attached to the porphyrin at the 4-position. The resulting sensitizing dye will then contain all four pyridine quaternized with methyl tosylate to yield the tetraquaternary porphyrin, commercially available. This dye, known to be an excellent intercalating dye, also produces singlet oxygen, which will convert the enol ether to the desired dioxetane label. Irradiating the intercalated, precursor-labeled, hybridized probe with light in the presence of molecular oxygen will produce the singlet oxygen, to generate a dioxetane.

The photooxygenation of an enol ether to a corresponding dioxetane can be accomplished using other methods. For example, a polymer filter with a coating of a sensitizing dye placed over a surface containing a precursor labeled probe: nucleic acid hybrid can be irradiated in the presence of molecular oxygen to generate singlet oxygen. Many polymers in which oxygen can diffuse are suited for such filters, for example, gelatin.

Further, the sensitizing dye can be directly incorporated into a nucleic acid probe by enzyme insertion and thereby provide a proximity between the sensitizing dye and the dioxetane precursor.

Assay Protocols

A wide variety of assays can be designed using probes provided with dioxetane precursors which, after completion of the assay manipulative steps, are converted into dioxetanes, and then caused to decompose to release light. As a general matter, the labeled probe is hybridized with any target complementary sequence in the sample, if present, followed by standard hybridization stringency washings, the dioxetane in any remaining probe is formed, and then decomposed to release light. The light, its character and amount, is indicative of the presence and quantity of the labeled probe, and therefor, the target complementary sequence. Hybridization steps found in the art are used, without modification.

This format permits in-situ DNA detection of specific sequences in intact cells, or chromosomes. The dioxetane labeled probe is triggered, the triggering event, or chemiluminescence, to be detected with a microscope. Similarly, DNA detection may be achieved through this invention in gel sequence analysis, and related gel-based assays.

Protocol 1

Homogeneous Assay Using PCR Amplification

In this format, a probe is labeled with both a dioxetane precursor and a fluorescein or other energy transfer fluorescing receptor. A wide variety of modified fluorescing compounds suitable for energy transfer, as well as methods of modifying the same are set forth in U.S. Pat. No. 4,959,182. Others are known to those of skill in the art. See, e.g., PCT/US81/01286 and WO85/04958. During the PCR process, if this probe anneals to the target sequence, it will then be cleaved by Taq™ polymerase during elongation which will separate the dioxetane precursor label and the fluorescent energy acceptor. Following a set number of cycles, a photosensitizing dye is added and the sample is irradiated in the presence of oxygen to generate the dioxetane. Upon triggering of the dioxetane, no energy transfer will occur and blue emission of the dioxetane alone would be detected from the reacted probe. If the probe, however, does not anneal, then the signal will be emitted via the fluorescent acceptor with the accompanying wavelength shift in the green region. Thus, qualitation and quantitation is easily achieved.

Protocol 2

Homogeneous Assay Using PCR Amplification

Another approach to a homogeneous assay is to use dioxetane precursor labeled PCR primers in the PCR amplification and include in the PCR reaction the intercalating sensitizing dye.

In a quantitative PCR protocol, 5' end labeled PCR primers containing a sequence of interest, such as a viral sequence, are used. These are end labeled in the DNA synthesizer with a dioxetane precursor to produce a heat-labile dioxetane label. A microplate thermocycler with a CCD camera, enclosed to be light-tight, and capable of imaging a whole microplate in the thermocycler is provided. This instrument also includes a light irradiation source for the photooxygenation reaction. The light source is programmed to turn on at the end of the chain elongation cycle (low temperature end). Imaging of the thermally activated dioxetane occurs during the denaturing cycle.

The DNA samples, end labeled PCR primers, intercalating dye and other reagents required for PCR are added to the wells of a microplate for PCR. The plate is inserted to the instrument described. PCR is initiated by raising the temperatures for the amplification being performed. At the end of each elongation cycle, singlet oxygen is generated, and the dioxetane precursor on the labeled primers which have been elongated is converted to the dioxetane label. The chemiluminescent signal from the dioxetane label is detected during the denaturation (high temperature) cycle. The intensity of the signal is proportional to the amount of PCR product at the end of each cycle.

Protocol 3

Heterogeneous assays on Membranes, Beads or Microplate Solid Supports

The probe hybridization assays employ standard hybridization and wash steps. The assay may be microtiter plate, bead or membrane based, and alternative variations will occur to those of skill in the art. Nucleic acid probes are synthesized with dioxetane precursor labels, as described above. The sample is immobilized. Labeled probes (probes bearing dioxetane precursors) are hybridized to the complementary target nucleic acid sequences in the immobilized sample. Following hybridization, and stringency washes, the solid phase is incubated in the presence of intercalating dye, washed and exposed to a light source to generate singlet oxygen to form dioxetane labels from the precursor labels previously attached. In the alternative, an appropriate suspension including a sensitizing dye is prepared, and singlet oxygen is again generated. The resulting dioxetane may be sufficiently short lived so as to spontaneously decompose, or be easily decomposed by raising the pH, by heating, or other known techniques. The resulting chemiluminescent signal detected is indicative of both the presence, and amount of target complementary sequence present.

Protocol 4

Genetic Screening Assays Using Dioxetane Precursor Labeled Amplification Primers The surface of the microchip, or other miniaturized electromagnetically sensitive device can be provided with an array of the most common mutants or variants of a specific target DNA sequence. An exemplary target is cystic fibrosis (CF) mutations. 5' end labeled CF mutation specific PCR primers are prepared. These primers are labeled with a dioxetane precursor. Alternatively, PCR products are labeled by incorporation of dioxetane precursor labeled nucleotides during amplification. Usually, 10 to 50% of dioxetane precursor labeled dCTP is substituted for unlabeled dCTP in the PCR reaction, when using this method. A microchip is coated with capture oligonucleotide specific for the one-hundred most common CF mutations, and controls. DNA is isolated from an individual to be screened for CF. The DNA is amplified using multiple pairs of labeled CF primers and standard amplification methods known in the art. An aliquot of the PCR reaction is removed, the DNA denatured by heating to 95° C. for 5 minutes and chilled on ice, and placed into a hybridization buffer, 3M tetramethyl ammonium chloride. 25 mM Tris-HCl, pH 8.0, 1 mM EDTA, 0.25% Triton X-100. The products of the PCR reaction are hybridized with the CF coated microchip. This is accomplished by placing the chip in a liquid containing hybridization chamber or a flow cell for several hours at 37° C. Stringency washes are performed by rinsing the chip 4–6 times at ambient temperature with 6×SSPE (0.9 M NaCl, 50 mM NaPO$_4$, 5 mM EDTA, pH 7.5), 0.25 Triton X-100. Hybridization and wash conditions may vary depending on probes and target sequences. Following stringency washes, the chip is incubated with a solution of an intercalating phosphosensitizing dye, and rinsed to remove excess dye. Singlet oxygen is produced by irradiation with visible light in the presence of molecular oxygen. The chip is inserted into a CCD detection system. The dioxetane is triggered, or otherwise activated, by addition of a triggering reagent such as a base (e.g., sodium methoxide in methanol or DMSO) while simultaneously imaging the chemiluminescent signal.

Protocol 5

Identification of Cystic Fibrosis Mutations on Microchip Surfaces

Patient DNA is amplified using primers for CF gene regions with potential mutations. Primers tagged with T3 and T7 promoter sequences are utilized. After amplification, promoter tagged PCR products are used as templates in transcription reactions with T3 or T7 polymerase and dioxetane precursor labeled nucleotides. Dioxetane precursor labeled CTP is mixed with unlabeled CTP, 5–60% total. Labeled RNA is fragmented by adding MgCl$_2$ to 30 mM and heating to 94° C. for 40 minutes. After fragmentation, RNA is hybridized to a microchip containing an array of oligonucleotides representing all potential mutations in the CF gene regions amplified. Hybridization is performed by placing the chip in a flow cell or hybridization chamber at 37° C. which contains the RNA sample diluted in hybridization buffer (3M tetramethyl ammonium chloride, 25 mM Tris-HCL pH 8.0, 1 mM EDTA, 0.25% Triton X-100) for 3 hours. Stringency washing is performed by rinsing the chip 4–6 times at room temperature with 6×SSPE (0.9 M NaCl, 50 mM NaPO$_4$, 5 mM EDTA, pH 7.5), 0.025% Triton X-100. Following stringency washes, the chip is incubated with a solution of intercalating photosensitizing dye, and rinsed to remove excess dye. Dioxetane is produced on the chip by irradiation with visible light and production of singlet oxygen. Alternatively, a nonintercalating dye is incubated with the chip with concurrent induction of singlet oxygen and dioxetane production by irradiation with visible light. The chip is placed in a CCD detection system. The dioxetane is triggered, or otherwise activated, by addition of a triggering reagent such as base (0.4 M NaOMe in DMSO) while simultaneously imaging the chemiluminescent signal.

Protocol 6

Alternative Polynucleotide Labeling Protocol

Oligonucleotides, PCR products, RNA and enzymatically labeled long double stranded probes are labeled by first incorporating a reactive amine into the probe or target followed by reaction with an activated form the dioxetane precursor. Oligonucleotides are labeled with a primary amine through commercially available amine functionalizing phosphoramidites or CPG columns. PCR products and RNA transcripts are labeled with reactive amines by incorporating amine labeled deoxyribonucleotide or ribonucleotide triphosphates, respectively, into PCR amplification reactions or transcription reactions. Random primer reactions or nick translation reactions, known to those skilled in the art, are modified to incorporate amine functionalized nucleotides. Each of the products are labeled with dioxetane precursor and hybridized, specifically attached to a solid support, or used in a homogeneous assay using the same protocols as described previously.

This invention also pertains to assays formatted with antibodies labeled with dioxetane precursors. The dioxetane precursor labeled antibodies are then used to quantitate the amount of analyte captured by an immobilized antibody on a solid phase such as a microwell, microparticle on silicon chip. After incubation with the dioxetane precursor labeled antibody, and washing, a solution of sensitizing dye is added and the sample is irradiated to generate singlet oxygen to form the dioxetane. The dioxetane is then triggered in an instrument such as a luminometer.

A sandwich immunoassay can also be designed with photosensitizing dye labeled capture antibody immobilized on a solid phase. After incubation with an antigen containing sample and a dioxetane labeled detector antibody, the sample is irradiated to form the dioxetane. The dioxetane is then triggered and the light signal detected.

Protocol 7

A Quantitative Sandwich Immunoassay Using Dioxetane Precursor Labeled Detection Antibodies This type of assay utilizes a format of a nylon bead coated with an anti-TSH monoclonal antibody to capture TSH from a serum sample. After washing, the bead is incubated with a different anti-TSH monoclonal antibody labeled with a precursor to a base triggerable dioxetane. The bead is then washed, incubated wish a solution of a sensitizing dye (such as methylene blue) and irradiated with light to generate singlet oxygen and subsequently the dioxetane. A base solution is then added to the bead to trigger the dioxetane and the signal detected with a luminometer. The intensity of the chemiluminescent signal is proportional to the amount of TSH in the sample.

Protocol 8

A Quantitative Sandwich Immunoassay Using Dioxetane Precursor Labeled Detection Antibodies and Sensitizer Dye Labeled Capture Antibodies This type of assay is formatted to use a nylon bead coated with a methylene blue labeled anti-TSH monoclonal antibody to capture TSH from a serum sample. The sample is simultaneously incubated with a different anti-TSH monoclonal antibody labeled with a precursor to a base triggerable dioxetane. The sample is then irradiated with light and only the dioxetane precursor on the antibodies attached to the TSH immobilized by the solid phase bound, methylene blue labeled anti-TSH is converted to a dioxetane. The sample is then treated with base to trigger the dioxetane and the signal is detected with a luminometer. The intensity of the chemiluminescent signal is proportional to the amount of TSH in the sample.

Protocol 9

A Microchip Based Determination of Allergic Response

An assay is designed for allergy testing by coating defined areas of a microchip with a set of allergens. The chip is then incubated with a patient's serum sample followed by incubation with a dioxetane precursor labeled anti-human IgE antibody. The chip is then flooded with a solution of sensitizing dye (such as methylene blue) and irradiated with light to form the dioxetane. The dioxetane is subsequently triggered and the light signal detected with a CCD. The spatially defined signal is indicative of the patient's allergies.

Protocol 10

A Gel Migration Study of Labeled Binding Events

A widely used, fundamental analysis comprises gel migration assays. In these assays, a sample to be inspected is deposited on a hydrated gel. The gel, and sample, are subjected to one or more influences which cause the components of the sample to migrate through the gel differentially, to permit isolation and analysis of the sample components. Applied influences most commonly include application of an electric field along the length of the gel. Additional influences can include secondary electric or magnetic fields, as well as various selective solvents.

Gel assays can be used in connection with this invention to determine the presence of specific binding events. Thus, one way to quickly isolate a target material, as well as to confirm its presence and quantify the same, is to combine a sample with the labeled probe. For binding assays, this will typically be a protein, either an antibody specific for a protein target suspected to be present in the sample, or an antigen which will be bound by an antibody whose presence is suspected in the sample, such as an autoantibody, or an antibody raised to a specific pathogen. Antibodies specific for target steroids or carbohydrates can alone be employed, as is true of protein-based assays described above. The probe is labeled with a dioxetane precursor. The probe and sample are combined under conditions which permit binding therebetween. Nucleic acids, and peptide nucleic acids may be similarly used as probes, for studies of binding events.

After sufficient time for binding, the sample combined with the probe is deposited on the gel, and subjected to forces inducing migration, including electric potentials. After migration is completed, according to the assay protocol, the precursor attached to the probe is converted to a 1,2-dioxetane, by exposure to singlet oxygen. A preferred method for generating singlet oxygen in a gel, such as a polyacrylamide gel, polyacrylamide/urea cross-linked gel, and the like, or other suitable gel (e.g., agarose) is by use of a polymer filter, as described above, with a coating of sensitizing dye placed over the surface of the gel in the presence of molecular oxygen. In the alternative, the gel itself may serve as the filter, in which molecular oxygen is diffused. This is described in more detail above.

Upon formation of the dioxetane moiety bound to the probe, which, in addition to being an antibody for a protein, may be an antibody for a steroid or carbohydrate, as desired, one or more conditions are altered to cause the dioxetane moiety to decompose, and generate light. This condition, or "trigger", can be selected from a wide variety of alternatives. For gel-based assays, alteration of pH, or heat, to induce decomposition and chemiluminescence, are preferred triggers.

It should be noted that as an alternative method of generating singlet oxygen, as described above, where the probe comprises a nucleic acid, a sensitizing dye, as is described above, is allowed to intercalate in the probe. This preferably occurs subsequent to binding/hybridization. After migration, the dye is irradiated with light (photooxygenized) to produce singlet oxygen, again generating the dioxetane.

Protocol 11

Gel-Based Assays Without Binding or Hybridization

Many assays conducted on gels, particularly electrophoretic assays, are not dependent on hybridization, or a binding event. This invention embraces the use of non-biological "probes" used as reference markers, to allow the practitioner to determine the presence of a particular target compound in a sample or gel, isolate it, and analyze it if required.

This assay can take many forms. One popular assay is a size base sequence analysis. In this assay, a polynucleotide, or nucleic acid fragment, is digested by a variety of restriction enzymes, to produce smaller fragments, which allow practitioners to construct a "gene map" of the corresponding polynucleotide. Separation and identification of each fragment produced is commonly performed with radioactivity. After the fragments have been produced, by enzymatic digestion, a 1,2-dioxetane precursor can be indiscriminately attached to the terminal end of all fragments. As a general matter, each fragment will have a different migratory character. After allowing migration to go forward, to achieve separation, the dioxetane precursor bound to the terminal end of each fragment is converted into a dioxetane moiety bound to the fragment, by exposure to singlet oxygen, as described above. Again, this is preferably affected by the use of a polymer filter, or by the use of intercalating sensitizing dye. The 1,2-dioxetanes are then triggered, preferably by alteration of pH, application of mild heating, or another appropriate trigger. The chemiluminescence released is monitored by a camera, film or other light-sensitive instrument. Separate flashes of chemiluminescence identifies separate fragments of distinct chemical composition, which, if required, may be separately eluted from the gel, and analyzed.

An alternative assay not dependent on hybridization or binding is one that searches for a specific compound whose presence is suspected in the sample being investigated. Thus, a wide variety of drugs, both pharmaceutical and non-pharmaceutical, have characteristic migration patterns in specific gel-based assays. There are non-drug happens, whose migration character can also be obtained as reference data. These drugs and non-drug haptens can be functionalized with a dioxetane precursor. The probe is added to the sample, and placed on the hydrated gel, and subjected to electrophoresis or other migratory influence. After a suitable time for separation, the precursor on the probe present is converted to the dioxetane, by exposure to singlet oxygen, as above. Subsequent application of a trigger such as a change in pH, or application of mild heating, induces decomposition of the 1,2-dioxetane bound to the "probe", releasing chemiluminescence. The chemiluminescence is monitored by a camera, film or other light-sensitive device. That portion of the gel where chemiluminescence is detected is removed, and sample components present therein are eluted, to determine whether the corresponding target compound is present in the sample. This gel-based protocol permits assays for multiple "target" compounds at one time, by using a variety of precursor-labeled "probes" having different migration parameters. This reduces the time and cost involved in a battery of assays, typically encountered in forensic pathology and the like.

Protocol 12

Capillary Zone Electrophoresis

Capillary Zone Electrophoresis (CZE) is an assay format that takes advantage of the different rates of migration that different components of a sample exhibit in a liquid medium under applied forces, including electric and magnetic fields. A sample is introduced into an apparatus including a capillary, where components of different charge and/or size will migrate through the capillary zone at different rates. As the material migrates to the end of the capillary, that fraction corresponding to the migration rate of the target(s) is collected, for inspection and analysis, if required. This requires significant reference data be developed.

The labeled probes of this invention can be advantageously used in binding and non-binding CZE. In an assay, employing probes which bind to the target, such as nucleic acids or peptide nucleic acids which hybridize with complementary target sequences, or antibody or antigen probes specific for proteins, carbohydrates, steroids or antibodies, the probe is prepared substantially as described above. Specifically a 1,2-dioxetane precursor is bound, either covalently or through a ligand bond such as an avidin/biotin complex. The probe is mixed with the sample under conditions which permit the probe to bind any target present. Unbound probe may be removed.

The combined sample is introduced to the CZE apparatus. The bound 1,2-dioxetane moiety is formed through exposure to singlet oxygen. If the 1,2-dioxetane moiety bound to the probe is sufficiently stable to persist throughout the assay, it may be formed prior to introduction to the CZE apparatus. In the alternative, non-stable 1,2-dioxetanes may be formed in a region of the CZE apparatus immediately prior to the exit/fraction collection point, then caused to chemiluminesce. Triggers useful in such assays are typically thermal, or pH based.

In an alternative embodiment, a reference component, corresponding to the target, is prepared with the bound 1,2-dioxetane precursor label. Again, this precursor can be converted to the corresponding dioxetane at any point. The labeled reference component is added to the sample and introduced to the CZE system. If not previously formed, the 1,2-dioxetane moiety is formed from the precursor by exposure to singlet oxygen. Immediately prior to the exit of the capillary, a zone is prepared in which decomposition of the 1,2-dioxetane moiety with will be induced, for example by heating, or acid/base addition. This zone is monitored for chemiluminescence. Observed chemiluminescence indicates that the target component, if present, will be in the next inspection fraction, making isolation and analysis easy without preparation of reference data.

Other protocols will occur to those of skill in the art.

The dioxetane precursor labels, the labeled probes, the assay protocols described herein have been described both generically, and by specific example. Dioxetanes which are thermally triggerable, chemically triggerable (e.g., by pH change) and triggerable by other means are known to those of skill in the art. These dioxetane structures can be adapted, by appropriate selection of substituents on the dioxetane precursor, so as to provide for an assay format which uses the thermal triggering, chemical triggering, etc., to generate the chemiluminescent signal, without the exercise of inventive faculty. Similarly, modification of the assay protocols set forth will occur to those of skill in the art, to adapt the inventive assay and products to a specific situation. These modifications employ the spirit of the invention, and remain within the scope of the invention, unless specifically excluded by the recitation of the claims set forth below.

What is claimed is:

1. A composition of matter comprising:
   a support which comprises an inspectible surface;
   a plurality of oligonucleotides provided on said surface,
   wherein at least one oligonucleotide of said plurality of oligonucleotides is bonded to a chemiluminescent dioxetane precursor, which precursor can be converted to a chemiluminescent dioxetane moiety which can be triggered to chemiluminesce.

2. The composition of matter of claim 1, wherein said plurality of oligonucleotides includes nucleotides of different base sequences.

3. The composition according to claim 1, wherein said precursor is selected from the group consisting of an enol ether and a phosphonate ester.

4. The composition according to claim 1, wherein said oligonucleotide is bonded to said precursor either directly or through a linker group.

5. The composition according to claim 1, wherein said oligonucleotide is bonded to said precursor directly.

6. The composition according to claim 1, wherein said oligonucleotide is bonded to said precursor through a linker group.

7. The composition according to claim 1, wherein said oligonucleotide remains bonded to said chemiluminescent moiety after said precursor is converted to said chemiluminescent moiety.

8. The composition according to claim 1, wherein said precursor has the formula (I):

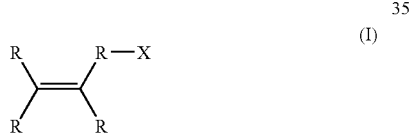

(I)

wherein each R is independently a hydrogen or $C_{1-20}$ group selected from the group consisting of alkyl, heteroalkyl, heteroaralkyl, cycloalkyl, aryl, heteroaryl, substituted aryl, hydroxyaryl, substituted hydroxyaryl, acyloxyaryl, substituted acyloxyaryl, aralkyl, aryloxy, silyloxyaryl, substituted silyloxyaryl, aminoaryl, substituted aminoaryl, sulfonamidoaryl, and substituted sulfonamidoaryl,
wherein any two of said R groups may be joined together to form one or more rings,
wherein X is selected from the group consisting of a direct bond to said oligonucleotide, and a linking group bonded to said oligonucleotide.

9. The composition according to claim 8, wherein X is a linking $C_{1-11}$ alkyl group, which is optionally substituted, and which optionally comprises at least one heteroatom, and wherein said X is attached to the -R- group in the formula with a carbon-carbon bond or a carbon-heteroatom bond.

10. The composition according to claim 8, wherein X is a linking $C_{1-6}$ alkyl group, which is optionally substituted, and which optionally comprises at least one heteroatom, and wherein said X is attached to the -R- group in the formula with a carbon-carbon bond or a carbon-heteroatom bond.

11. The composition according to claim 8, wherein at least one R group has the formula —OY, wherein Y is aryl, alkyl, aralkyl, and cycloalkyl.

12. The composition according to claim 8, wherein each R group has an allylic carbon bonded to the double bond in formula (I), and wherein none of the R groups have a proton bonded to the allylic carbon.

13. A composition of matter comprising:
   a support which comprises an inspectible surface;
   a plurality of oligonucleotides provided on said surface,
   wherein at least one oligonucleotide of said plurality of oligonucleotides is bonded to a chemiluminescent dioxetane precursor, which precursor can be converted to a chemiluminescent dioxetane moiety which can be triggered to chemiluminesce,
   wherein said chemiluminescent dioxetane moiety comprises a protective group which, if removed, induces decomposition of said chemiluminescent moiety to produce chemiluminescence.

14. The composition according to claim 1, wherein said chemiluminescent moiety is bonded to said oligonucleotide either directly or through a linking group.

15. The composition according to claim 1, wherein said chemiluminescent moiety is bonded to said oligonucleotide through a linking group.

16. The composition according to claim 1, further comprising at least one sensitizing dye.

17. The composition of claim 1, wherein the chemiluminescent dioxetane precursor has the following structure:

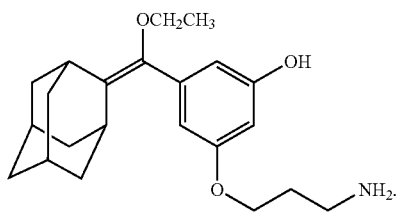

18. The composition of claim 1, wherein the chemiluminescent dioxetane precursor can be converted to a chemiluminescent dioxetane moiety via oxidation.

19. A method of detecting the presence of a nucleic acid of predetermined sequence in a sample, comprising exposing the composition of matter of claim 1 to said sample under conditions which promote the hybridization of said nucleic acid of predetermined sequence to at least one of said oligonucleotides, and inspecting said surface after any hybridization event may have occurred, where hybridization is indicated by release of chemiluminescence from the support.

20. The composition according to claim 1, wherein the chemiluminescent moiety is bonded to the oligonucleotide directly.

* * * * *